United States Patent [19]

Törmälä et al.

[11] Patent Number: 4,968,317

[45] Date of Patent: Nov. 6, 1990

[54] SURGICAL MATERIALS AND DEVICES

[76] Inventors: Pertti Törmälä, Reikonkatu 7 C 7, SF-33730, Tampere, Finland; Pentti Rokkanen, Marjaniemenranta 29, SF-00930, Helsinki, Finland; Seppo Vainionpää, Orapihlajhatie 21-27 B 12, SF-00320, Helsinki, Finland; Juha Laiho, Pirkankatu 20 B 1 SF-33230, Tampere, Finland; Veli-Pekka Heponen, Hallituskatu 15 B 37 SF-33200, Tampere, Finland; Timo Pohjonen, Mekaniikanpolku 18 B 19 SF-33720, Tampere, Finland

[21] Appl. No.: 250,039

[22] PCT Filed: Dec. 29, 1987

[86] PCT No.: PCT/FI87/00177

§ 371 Date: Oct. 14, 1988

§ 102(e) Date: Oct. 14, 1988

[87] PCT Pub. No.: WO88/05312

PCT Pub. Date: Jul. 28, 1988

[30] Foreign Application Priority Data

Jan. 13, 1987 [FI] Finland ................... 870111

[51] Int. Cl.$^5$ ............................................. A61B 17/58
[52] U.S. Cl. .......................................... 606/77; 606/76
[58] Field of Search ...................... 128/924 R, 924 Q; 606/76, 77

[56] References Cited

U.S. PATENT DOCUMENTS

| | | | |
|---|---|---|---|
| 3,902,497 | 9/1975 | Casey | 128/325 X |
| 4,128,612 | 12/1978 | Roth | 128/325 X |
| 4,263,185 | 4/1981 | Belykh et al. | 128/92 YR X |
| 4,604,097 | 8/1986 | Graves, Jr. et al. | 623/18 X |
| 4,610,688 | 9/1986 | Silvestrini et al. | 623/1 |
| 4,612,923 | 9/1986 | Kronenthal | 128/92 Y R |
| 4,643,734 | 2/1987 | Lin | 623/16 |
| 4,655,203 | 4/1987 | Tormala | 128/89 A X |
| 4,743,257 | 5/1988 | Tormala | 128/92 Y R X |
| 4,781,183 | 11/1988 | Casey et al. | 128/92 Y R X |
| 4,792,336 | 12/1988 | Hlavacek et al. | 623/66 X |

FOREIGN PATENT DOCUMENTS

| | | | |
|---|---|---|---|
| 11528 | 5/1980 | European Pat. Off. | 128/92 Y R |
| 146398 | 6/1985 | European Pat. Off. | 128/92 Y R |

Primary Examiner—Robert A. Hafer
Assistant Examiner—Kevin G. Rooney
Attorney, Agent, or Firm—Pollock, Vande Sande & Priddy

[57] ABSTRACT

Surgical material of resorbable polymer, copolymer, or polymer mixture containing at least partially fibrillated structural units, and use thereof.

8 Claims, 8 Drawing Sheets

SURGICAL MATERIALS AND DEVICES

Surgical implants with good mechanical strength properties can be manufactured of resorbable polymeric materials (resorbable composites) which contain resorbable reinforcing elements. Resorbable or absorbable means in this connection that the material is metabolized by living tissues. Such resorbable materials and implants manufactured of them can be applied e.g. as rods, plates, screws, intramedullary nails etc. for fixation of bone fractures, osteotomies, arthorodesis or joint damages. An advantage of such implants and materials is that they are resorbed (depolymerized to cell nutrients) after the healing of the treated tissue. Therefore the resorbable implants do not need a removal operation, like metallic implants in many cases need.

Invention U.S. Pat. No. 4,279,249 describes resorbable implant materials comprising polyglycolide fibers as reinforcement and polylactide as a binding polymer (as a resorbable matrix). In the patent application FI No. 851 828 are described self-reinforced resorbable materials, where the resorbable polymer matrix has been reinforced with resorbable reinforcement elements which have the same chemical element content as the matrix. Typical reinforcement elements in this connection are fibers or structures which have been constructed of them.

The known resorbable materials reinforced with resorbable organic reinforcement elements have fairly high mechanical strength values. Therefore, such materials can be applied in orthopedics and traumatology in treatment of cancellous bone fractures, osteotomies, arthrodesis or joint damages. For example the self-reinforced resorbable materials of FI No. 851 828 describe bending strengths over 300 MPa (S. Vainionpää, Thesis, Helsinki 1987), which values clearly are higher than even the average strength values of cortical bone. Also the elastic moduli of known self-reinforced resorbable composites are quite high, typically of the order of magnitude of 10 GPa. So the strength values of these materials are clearly better than those of resorbable materials which have been manufactured by melt molding techniques.

When one manufactures resorbable polymers, co-polymers or polymer alloy rods, profiles, plates, etc. implants by melt molding techniques like by injection molding or by extrusion, the mechanical properties of the products remain on the level which is typical for thermoplastic polymers. The strength values (like tensile, shear and bending strength) typically do not exceed the value 150 MPa showing, typically, strength values between 40 and 80 MPa and moduli between 1 and 6 GPa. The reason for this behavior is the fact that the flow orientation which exists in the flowing polymer melt is relaxed as a consequence of molecular thermal movements when the melt molded sample is cooled. When it is a question of a crystallizable polymer, the sample is crystallized to a partially crystalline, spherulitic structure. So the polymeric material manufactured by melt molding typically consists of folded crystalline lamellae (the thickness 100–300 Å, the breath about 1 $\mu$m), which are surrounded by the amorphous polymer. On the other hand, the lamellae can be thought to consist of mosaic-like folded blocks (the breadth of some hundreds of Å). The lamellae, as a rule, form ribbon-like structures which grow from crystallization centers, so-called nuclei, to three-dimensional spherical spherulitic structures. Because the polymer material which has been crystallized with the spherulitic mechanism does not show, as a rule, significant orientation of polymer molecules with strong covalence bonds, its mechanical strength values remain on the above mentioned level. Only on the surface of the sample molecular orientation can remain because of rapid cooling in the mold (as in the case of injection molding).

Although the reinforced resorbable composites show considerably better strength properties than melt molded resorbable composites, it is often necessary to manufacture of resorbable reinforced composites quite big implants, like rods, intramedullary nails, screws or plates. This is necessary because one must secure for the load carrying capacity (like bending or shear load carrying capacity) of the implants a security marginal high enough to confirm the stability of the fixation also in such a case when outer stresses or muscle stresses are directed to the fixated fracture, osteotomy, arthrodesis or joint damage, because the above mentioned stresses can clearly exceed the weight of the patient. On the other hand, such big implants which the security of the patient demand, cause quite big operative traumas to the bone tissue and/or to the soft tissues when the implant e.g. is located into a drill-hole which has been drilled into the bone or the implant is fastened on the surface of the bone. With the increasing size of the implant the possibilities to a foreign body reaction increase, the reaction may grow stronger or its duration may be prolonged because the implant and the resorption of the implant cause to the living tissues physical and chemical stresses which are in a direct correlation to the size of the implant.

So far, the elastic modulus values of resorbable implants which have been manufactured of organic materials are at the best the order of magnitude of 10 GPa. This is a lower level of elastic modulus than the elastic moduli of cortical bones, which are typically the order of magnitude of 20 GPa and can even exceed 30 GPa. When the main goal of the surgeon is as good fixation as possible it is advantageous if the elastic modulus of the implant is as near as possible of the elastic modulus of the bone. In the ideal case the elastic moduli of the bone to be operated and of the implant are equal. Therefore it is evident that an efficient fixation of cortical bone, like long bones, needs resorbable organic composite materials which have higher elastic modulus values than those of the known materials.

In this invention we have found unexpectedly that by increasing the strength and elastic modulus values of resorbable polymeric materials by orientation of the molecular structure of the material in such a way that it is at least partially fibrillated, we get new macroscopical resorbable self-reinforced implant materials, which have considerably higher strength and elastic modulus values than those of the known resorbable implant materials. When the materials of this invention are applied as surgical fixation materials, -devices or in manufacturing of such devices one can effectively decrease the operative trauma which the implant causes and at the same time one can obtain significantly better fixation than with the known materials. This invention describes at least partially fibrillated (a) fixation materials for treatment of bone fractures, osteotomies, arthrodesis or joint damages, (b) materials for reconstruction and augmentation of bone tissue and (c) the fixation devices, reconstruction devices and augmentation devices like rods, plates, screws, intramedullary nails, clamps and chutes manufactured at least partially of the above materials using as raw material resorbable polymer, copolymer or polymer mixture. Further this invention describes the application of at least partially fibrillated resorbable materials and especially the application of rods, plates, screws, intramedullary nails, clamps or chutes manufactured of the above mentioned materials in fixation of bone fractures, osteotomies, arthrodesis or joint damages or in augmentation or reconstruction of bone tissue.

The orientation and fibrillation of spherulitic polymer systems is a process, which has been studied extensively in connection with the manufacturing of thermoplastic fibers. E.g. the invention U.S. Pat. No. 3,161,709 describes a three phase drawing process, where the melt molded polypropylene filament is transformed to a fiber with high mechanical tensile strength.

Figure 1A:
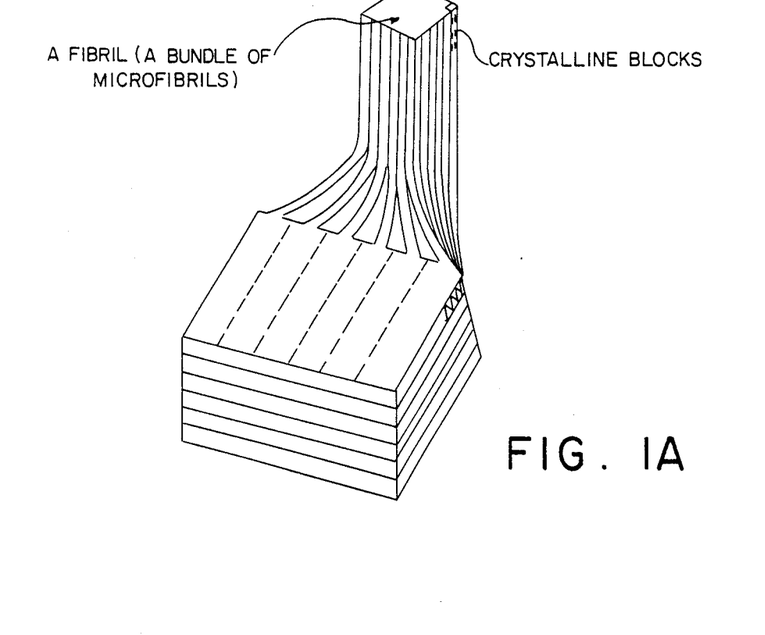
Figure 1B:
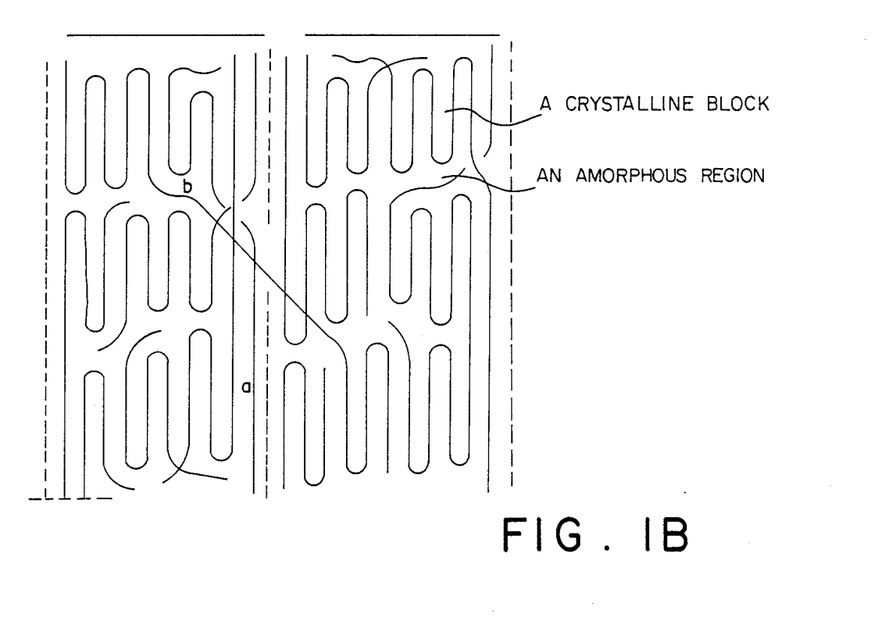
Figure 1C:
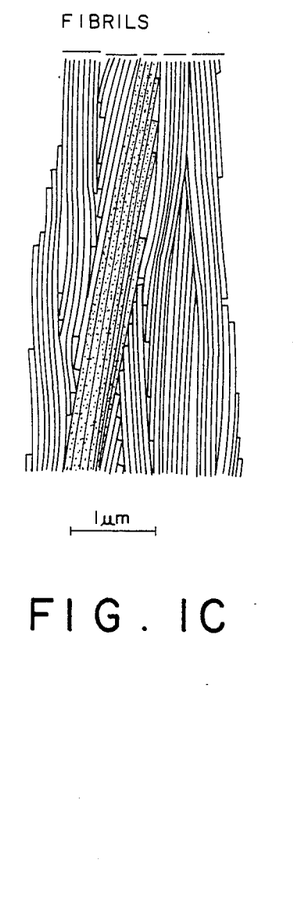

The mechanism of the fibrillation is of its main features the following one (C. L. Choy et al. Polym. Eng. Sci., 23 1983, p. 910). When a semicrystalline polymer is drawn, the molecular chains in the crystalline lamellae are aligned rapidly along the draw direction. At the same time, the spherulites are elongated and finally broken up. Crystalline blocks are torn off from the lamellae and are connected by taut tie-molecules originating from partial unfolding of chains. The alternating amorphous and crystalline regions, together with the taut tie-molecules, therefore, form long, thin (ca. 100 Å width) microfibrils which are aligned in the draw direction. Since the intrafibrillar tie-molecules are created at the interfaces between crystalline blocks, they lie mainly on the outside boundary of microfibrils. Tie-molecules which linked different lamellae in the starting isotropic material are now connecting different microfibrils, i.e., they become interfibrillar tie-molecules locating at the boundary layers between adjacent microfibrils. FIG. 1a shows, schematically, how a group of lamellae is transformed to a fibrillar structure (to a fibril which comprises a group of microfibrils) as a consequence of drawing, and FIG. 1b shows schematically the molecular structure inside of microfibrils and between them. FIG. 1c shows, schematically, the structure of fibrillated polymer. This Figure shows several fibrils (one of them has been colored grey because of clarity) which comprise several microfibrils with the length of several micrometers.

The fibrillar structure is already formed at relatively low draw ratios $\lambda$ (where $\lambda$ = the length of the sample after drawing/the length of the sample before drawing). E.g. HD-polyethylene is clearly fibrillated with the $\lambda$ value of 8 and polyacetal (POM) with the $\lambda$ value of 3.

When the drawing of the fibrillated structure is further continued (this stage of the process is called often ultra-orientation), the fibrillar structure is deformed by shear displacement of microfibrils, giving rise to an increase in the volume fraction of extended interfibrillar tie-molecules. If the drawing is performed at high temperature, the perfectly aligned tie-molecules will be crystallized to form axial crystalline bridges connecting the crystalline blocks.

The excellent strength and elastic modulus values of the fibrillated structure are based on the strong orientation of polymer molecules and molecular segments into the direction of the drawing (into the direction of the long axis of microfibrils).

Regardless of the high tensile strength of fibrillated fibers they cannot be applied as fixation devices of bone fractures, osteotomies, arthrodesis or joint damages, because thin fibers are flexible and, therefore, they do not show macroscopical bending strength and bending modulus and because of their small cross-sectional area they do not have the necessary shear load carrying capacity which the macroscopical fixation device must have.

Fibrillation of macroscopical polymeric samples, like rods and tubes, is known earlier in the case of biostable polyacetal and polyethylene (see e.g. K. Nakagawa and T. Konaka, Polymer 27, 1986, p. 1553 and references therein). However, the fibrillation of macroscopical samples of resorbable polymers has not been known earlier.

At least partial fibrillation of a macroscopical polymer sample can be carried out e.g. by cooling in a capillary tube flowing polymer melt rapidly to the solid state in such a way that the molecular orientation of the flowing molecules cannot relax as a consequence of molecular motions to a total or partial state of random orientation.

More strong fibrillation and, therefore, also better mechanical properties can be achieved by a mechanical deformation (orientation) of macroscopical polymer samples. Usually such a mechanical deformation is done by drawing or by hydrostatic extrusion of material in such a physical condition (in solid state), where strong molecular structural changes of crystalline structure and amorphous structure to fibrillar state are possible. As a consequence of fibrillation the resorbable polymeric material which has been manufactured e.g. by the injection molding or extrusion and which material initially is mainly spherulitic of its crystalline structure, changes first partially and later on totally to a fibrillated structure which is strongly oriented in the direction of drawing or of hydrostatic extrusion. Such a resorbable material consists, among other things, of oblong crystalline microfibrils and of tie-molecules connecting microfibrils and of oriented amorphous regions. In a partially fibrillated structure the amorphous regions between microfibrils form a more significant part of the material than in an ultraoriented material where in the extreme case amorphous material exists only as crystal defects around the ends of the polymer molecule chains. When the degree of fibrillation increases in a material its strength and elastic modulus values increase many times in comparison to the same values of non-fibrillated material.

Figure 2:
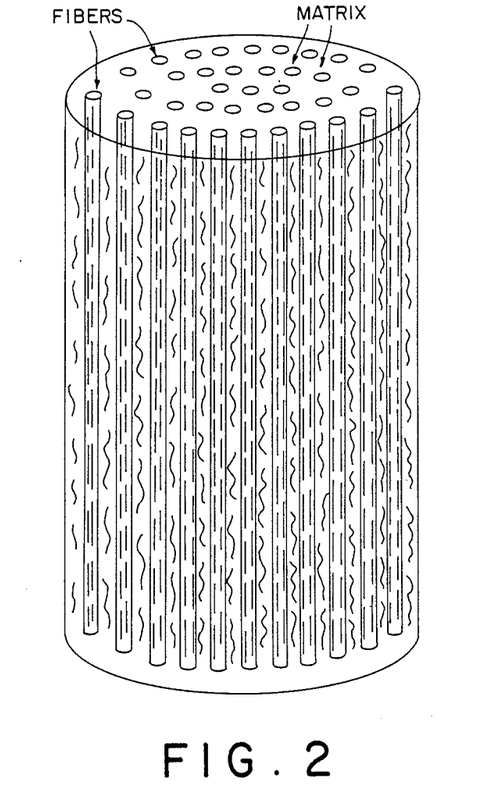

Known resorbable composite materials comprise typically randomly oriented (non-oriented) binding material phase (matrix), which binds to each other reinforcing elements like fibers which have strongly oriented internal structure. Such a structure has been shown schematically in FIG. 2, where oriented and non-oriented molecular chains or their parts have been described with thin lines. The strength properties of the binding phase are significantly weaker than the strength properties of the reinforcement elements. Therefore, the strength properties of the composite in the direction of orientation of reinforcement elements increase when the amount of reinforcement elements in the material is increased. As a consequence of practical difficulties the amount of reinforcement elements cannot exceed ca. 70 weight-% of the weight of the composite. Therefore, the strength properties of reinforcement elements cannot be utilized totally, because the composite contains also the weaker matrix material, which also contributes of its part to the total strength of the composite.

By means of orientation and fibrillation it is possible to manufacture of resorbable polymers, copolymers and polymer alloys self-reinforced composites, where nearly the whole mass of material has been oriented in a desired way and where the amount of the amorphous phase is small. Therefore, these materials show very high mechanical strength properties in the direction of orientation: tensile strength even 1000–1500 MPa and elastic modulus 20–50 GPa. Accordingly these strength values are clearly better than those of known resorbable composites and even about ten times higher than the strength values of melt molded resorbable materials.

Figure 3:
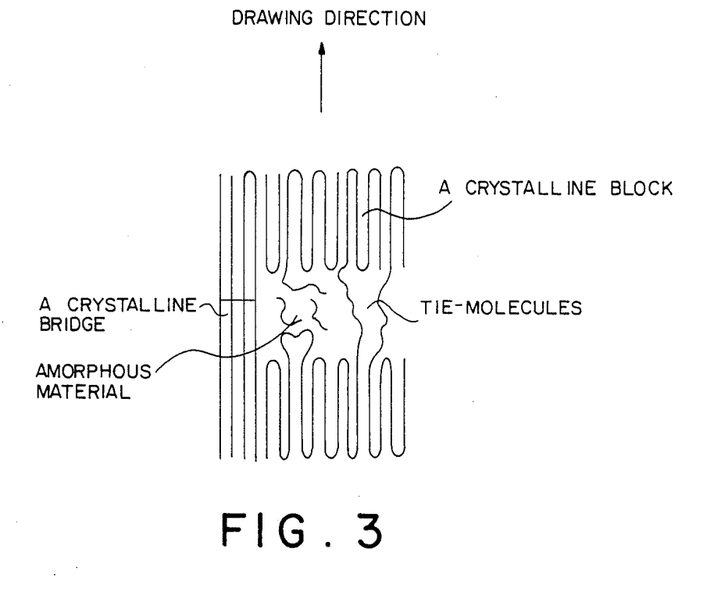
Figure 4A:
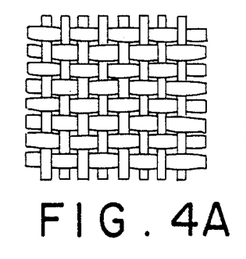
Figure 4B:
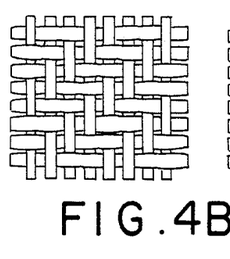
Figure 4C:
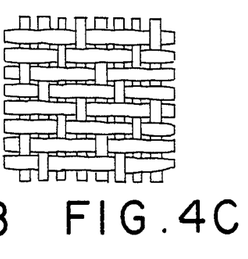
Figure 4D:
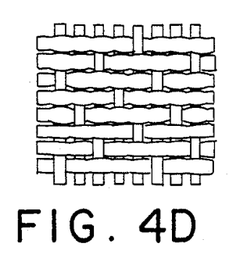
Figure 4E:
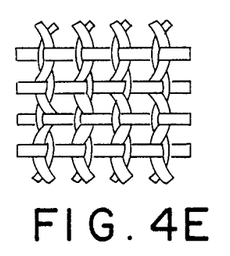

FIG. 3 shows schematically following structural units which can be seen in the fibrillated structure of polymer fibers and also in the structure of macroscopical, fibrillated polymer samples like rods and tubes: crystalline blocks which are separated from each other by amorphous material (e.g. free polymer chains, chain ends and molecular folds), tie-molecules, which connect crystalline blocks with each other (the amount and thickness of tie-molecules increases with increasing draw ratio $\lambda$) and possible crystalline bridges between crystalline blocks. Bridges can be formed during drawing when tie-molecules are oriented and grouped themselves to bridges (C. L. Choy et al. J. Polym. Sci., Polym. Phys. Ed., 19, 1981, p. 335–352).

The oriented fibrillated structure which is shown in FIGS. 1 and 3 develops already at so-called natural draw ratios 3–8. When the drawing is continued after this as an ultraorientation at a high temperature, the amount of crystalline bridges can increase very high and in the extreme case bridges and crystalline blocks form a continuous crystalline structure. The effects of tie-molecules and bridges are often similar and, therefore, their exact discrimination from each other is not always possible.

Orientation and fibrillation can be characterized experimentally by means of several methods. The orientation function $f_c$, which can be measured by means of x-ray diffraction measurements, characterizes the orientation of molecular chains of the crystalline phase. $f_c$ attains as a rule already at natural drawing ratios ($\lambda < 6$) the maximum value 1. The polymeric material with spherulitic structure shows $f_c << 1$.

Birefringence which can be measured by means of polarization microscope is also a quantity, which describes molecular orientation of molecular chains. As a rule it grows strongly at natural draw ratios ($\lambda < 6$) and thereafter during ultraorientation more slowly, which shows that the molecular chains of the crystalline phase are oriented into the drawing direction at natural draw ratios and the orientation of molecules in the amorphous phase continues further at higher draw ratios (C. L. Choy et al. Polym. Eng. Sci., 23, 1983, p. 910–922).

The formation of the fibrillated structure can be shown in many cases illustratively by studying the fibrillated material by means of optical and/or electron microscopy (see e.g. T. Konaka et al. Polymer, 26, 1985, p. 462). Even single fibrils which consist of microfibrils can be seen clearly in scanning electron microscopy figures which are taken of the fibrillated structure.

Table 1 shows some known resorbable polymers, which can be applied in manufacturing of resorbable materials and devices of this invention. A presupposition to an efficient fibrillation is, however, that the polymer exists in a partially crystalline form. Therefore, such polymers, which, because of their physical structure (e.g. configuration state), are not crystallizable, cannot be effectively fibrillated.

TABLE 1
Resorbable polymers

Polymer

Polyglycolide (PGA)
Copolymers of glycolide:
Glycolide/L-lactide copolymers (PGA/PLLA)
Glycolide/trimethylene carbonate copolymers (PGA/TMC)
Polylactides (PLA)
Stereocopolymers of PLA:
Poly-L-lactide (PLLA)
Poly-DL-lactide (PDLLA)
L-lactide/DL-lactide copolymers
Copolymers of PLA:
Lactide/tetramethylglycolide copolymers
Lactide/trimethylene carbonate copolymers
Lactide/$\sigma$-valerolactone copolymers
Lactide/$\epsilon$-caprolactone copolymers
Polydepsipeptides
PLA/polyethylene oxide copolymers
Unsymmetrically 3,6-substituted poly-1,4-dioxane-2,5-diones
Poly-$\beta$-hydroxybutyrate (PHBA)
PHBA/$\gamma$-hydroxyvalerate copolymers (PHBA/HVA)
Poly-$\beta$-hydroxypropionate (PHPA)
Poly-p-dioxanone (PDS)
Poly-$\sigma$-valerolactone
Poly-$\epsilon$-caprolactone
Methylmethacrylate-N-vinyl pyrrolidone copolymers
Polyesteramides
Polyesters of oxalic acid
Polydihydropyrans
Polyalkyl-2-cyanoacrylates
Polyurethanes (PU)
Polyvinylalcohol (PVA)
Polypeptides
Poly-$\beta$-malic acid (PMLA)
Poly-$\beta$-alkanoic acids Reference:
P. Tormala, S. Vainionpaa and P. Rokkanen in IVA's Beijer Symposium "Biomaterials and Biocompatibility", Stockholm, Sweden, August 25–26, 1987.

At least partially fibrillated and especially ultraoriented, resorbable polymer materials are an especially advantageous special case of oriented, self-reinforced resorbable composite materials where the oriented reinforcement elements (crystalline blocks, tie-molecules and crystalline bridges) form and/or group themselves during the mechanical deformation and where the phase which binds the above mentioned structural units is formed, among other things, of the following structural elements: amorphous phase, the interfaces between crystalline blocks and the interfaces between crystalline bridges and micrifibrils, which structural elements are also typically oriented strongly in the direction of deformation.

The resorbable, at partially fibrillated implant materials and osteosynthesis devices of this invention differ by several unexpected ways from known resorbable implant materials and devices. The materials and devices of this invention have as a consequence of strong orientation and of at least partially fibrillated structures excellent tensile-, bending- and shear strength properties and elastic modulus properties. This makes possible to apply in orthopedics and traumatology thinner and smaller rods, plates, screws, nails and clamps etc. than earlier is known. This decreases advantageously the operative trauma and the foreign body load caused by the implant to living tissues. Further the excellent mechanical strength- and elastic modulus properties make possible to apply the materials, implants and devices of this invention also in demanding fixation operations of long bone fractures, osteotomies and arthrodesis. It has been found also unexpectedly that the implants of this invention retain their mechanical properties in hydrolytic conditions longer than the implants of equal size which have been manufactured of the known materials. This makes it also possible to apply the materials and devices of this invention in treatment of such slowly recovering bone fractures, osteotomies and arthrodesis, where the known materials and implants cannot be applied.

The at least partially fibrillated rods, tubes, plates etc. profiles of this invention can be applied as such as fixation devices e.g. by the ways described in the inventions FI Pat. Nos. 69402 and 69403 or the materials can be formed to different kind of fixation devices like screws, rods with scaly covering and other profiled structures and clamps or other bended structures, because in this invention has been also found unexpectedly that the oriented resorbable materials can be hot-worked mechanically at high temperatures without loosening the fibrillated structure. This makes possible e.g. the manufacturing of especially strong and tough screws of the at least partially fibrillated rods of this invention.

It is natural that fibrillated resorbable materials can contain additionally different kinds of additives or auxiliary materials to make the processing of the material more easy (e.g. stabilizators, antioxidants or plasticizers) or to change its properties (e.g. plasticizers or powder-like ceramic materials) or to make its handling more easy (e.g. colours).

The stiff and strong resorbable fixation materials of this invention can be applied in the form of rods, plates or other profiles also in manufacturing of bigger fixation devices as reinforcement elements for example by packing into a cylindrical, oblong injection molding mold fibrillated rods and by filling the mould then by injecting into it suitable resorbable matrix polymer melt. When the injection is carried out from one end of the oblong mold, the injected melt flows in the direction of resorbable reinforcement elements. When the matrix material (polymer melt) flows and solidifies rapidly, into it is formed an advantageous orientation in the direction of the reinforcement elements.

The stiff and strong fixation rods or plates of this invention can be used also to construct stiff net-like and plate-like structures, which can resemble of their mechanical properties more metallic nets than nets which are manufactured of organic textile fibres. FIG. 4 shows schematically some types of net structures which are constructed of stiff, strong resorbable rods. Part of the rods has been described as white and part as black because of clarity. Such nets can be applied as such e.g. to treatment of comminuted fractures by combining the comminuted parts of broken bone to each other and by bending the net around the parts of broken bone to support it and by fixing the net e.g. with resorbable sutures or clamps. Such nets of this invention can be manufactured also e.g. by hot-pressing them to curved plates, chutes or box-like etc. corresponding structures, which can be applied to the reconstruction of bone etc. in such a way that a defect in bone tissue (a hole, a cavity, a cyst, etc.) is filled with tissue compatible ceramic powder like hydroxyapatite or tricalciumphosphate and the curved net is fixed on the defect to a cover, which immobilizes ceramic particles and prevents their movements from the defect. Because such nets of this invention are stiff they function in this connection as significantly more effective immobilizers than the known flexible nets which are manufactured of resorbable fibers.

Figure 5:
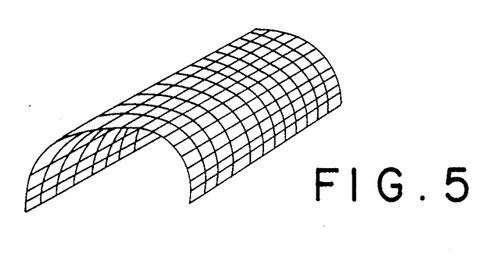
Figure 6:
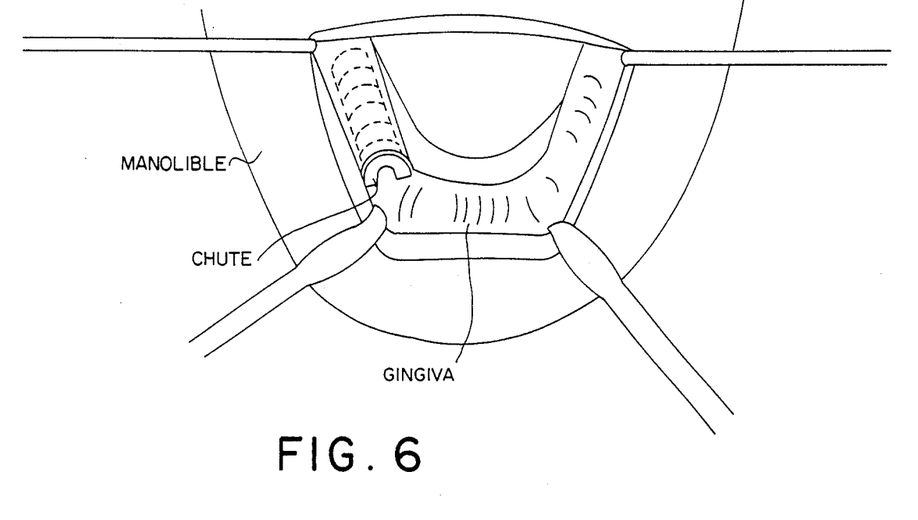

FIG. 5 shows schematically a net structure of this invention which is manufactured of resorbable rods and which has been bent to the form of a chute e.g. by hot pressing. Such a chute can be applied especially advantageously with ceramic materials to augmentation of bone tissue of alveolar ridges in the following way. First the subperiosteal tunnel is made surgically below the gingival tissue on the surface of the alveolar ridge. The resorbable tube is pushed inside of the tunnel in such a way that the convex surface of the chute is directed towards the gingival tissue and the end surfaces of the sides of the chute are placed on the alveolar ridge. This situation has been described schematically in FIG. 6 in the case of an operation which is done to the right side of the mandible. After installation of the chute it can be filled with ceramic bone graft powder and after that the operation incision can be closed. If necessary, it is possible to place on the same alveolar ridge several chutes after another. Such a chute prevents the movements of ceramic powder which has been packed below it. At the same time bone and connective tissue cells grow from the bone tissue of alveolar ridge and from the surrounding soft tissues into the ceramic powder by immobilizing it at last to a part of the bone tissue of alveolar ridge. The resorbable chute is resorbed at the same time or later.

Ceramic powders and pieces can be applied also in many other ways to augmentation or reconstruction of bone tissue (as bone graft materials).

Ceramic materials (bioceramics), which are tissue compatible and/or which form chemical bonds with bone tissue and/or which promote the growth of bone tissue, are e.g. calciumphosphate: apatites like hydroxyapatite, HA, $Ca_{10}(PO_4)_6(OH)_2$ (R. E. Luedemann et al., Second World Congress on Biomaterials (SWCB), Washington, D.C., 1984, p. 224), trade names like Durapatite, Calcitite, Alveograf and Permagraft; fluoroapatites; tricalciumphosphates (TCP) (e.g. trade name Synthograft) and dicalciumphosphates (DCP); magnesiumcalciumphosphates, S-TCMP (A. Ruggeri et al., Europ. Congr. on Biomaterials (ECB), Bologna, Italy, 1986, Abstracts, p. 86); mixtures of HA and TCP (E. Gruendel et al., ECB, Bologna, Italy, 1986, Abstracts, p. 5, p. 32); aluminiumoxide ceramics; bioglasses like $SiO_2$-CaO-$Na_2O$-$P_2O_5$, e.g. Bioglass 45S (structure: $SiO_2$ 45 wt-%, CaO 24,5%, $Na_2O$ 24,5% and $P_2O_5$ 6%) (C. S. Kucheria et al., SWBC, Washington, D.C., 1984, p. 214) and glass ceramics with apatites, e.g. MgO 4,6 wt-%, CaO 44,9%, $SiO_2$ 34,2%, $P_2O_5$ 16,3% and CaF 0,5% (T. Kokubo et al., SWBC, Washington, D.C., 1984, p. 351) and calciumcarbonate (F. Souyris et al., EBC, Bologna, Italy, 1986, Abstracts, p. 41).

The applications of the above ceramic materials as synthetic bone grafts have been studied by different means by using them, for example, both as porous and dense powder materials and as porous and dense macroscopical samples as bone grafts. Also ceramic powder - polymer composites have been studied in this means (e.g. W. Bonfield et al. SWBC, Washington, D.C., 1984, p. 77).

The resorbable strong and stiff materials of this invention can be applied in many different ways combined with porous bioceramics to biocomposites. The mechanical properties, especially the impact strength, bending strength and shear strength of such composites are significantly better than the corresponding properties of porous bioceramics. The invention FI Pat. Appl. No. 863573 describes several possibilities to combine resorbable polymeric materials and bioceramics. Those principles can be applied also when the materials of this invention are used in combination with bioceramics.

This invention has been illustrated by means of the following examples.

EXAMPLE 1

Poly-L-lactide (PLLA) ($M_w$=600.000) was injection molded to cylindrical rods with a diameter ($\phi$) 4 mm. The rods were drawn to the drawing ratio $\lambda$=7 at temperatures from room temperature to $T_m$−40° C. (where $T_m$=the melting point of the polymer). The fibrillated structure of the drawn rods was seen microscopically. Part of the rods was drawn further to a drawing ratio $\lambda$=12 (ultraorientation). As reference samples were sintered self-reinforced rods ($\phi$=1.5 mm) of PLLA fibers (tensile strength 800 MPa, $\phi$=15 μm) which rods were manufactured by a method described in FI Pat. Appl. No. 851828.

Following strength values were measured for the injection molded, fibrillated and sintered self-reinforced rods: tensile strength, elastic modulus and bending strength. The results of measurements are given in Table 1.

TABLE 1

Strength properties of PLLA rods

| Sample N:o | Manufacturing method | Rod thickness (mm) | Tensile strength (Mpa) | Elastic Modulus (GPa) | Bending strength (MPa) |
|---|---|---|---|---|---|
| 1 | Injection molding | 4 | 80 | 5.5 | 70 |
| 2 | Injection molding + fibrillation ($\lambda$ = 7) | 1.4 | 560 | 14 | 360 |
| 3 | Injection molding + fibrillation ($\lambda$ = 12) | 1.2 | 800 | 17 | 470 |
| 4 | Self-reinforcing (sintering) | 1.5 | 400 | 10 | 260 |

Table 1 shows that the strength properties of the fibrillated, resorbable rods of this invention are clearly better than the strength properties of the known resorbable materials.

EXAMPLE 2

Resorbable rods of Example 1 (the length 25 mm) were applied to fixation of the arthrodesis of the proximal phalanx of thumb by removing the both joint surfaces, by joining the uncovered bone surfaces temporarily to each other by clamps to an arthrodesis surface, by drilling through the arthrodesis surface two drilling channels and by tapping into the drilling channels the resorbable fixation rods. 20 patients had operations. The average area of the arthrodesis surfaces was ca. 170 mm². The calculatory shear load carrying capacity of the fixation was 1100N, when two fibrillated rods N:o 2 were applied. The proportion of drill channels (which describes the operative trauma) of the arthodesis surface was 1.8%. The corresponding values were for fibrillated rods N:o 3 1060N and 1.3% and for sintered rods N:o 4 920N and 2.1%. Accordingly the fibrillated rods give a stronger fixation than the sintered rods. Also the operative trauma was smaller in the case of the fibrillated rods. Injection molded rods were not applied in fixation, because they should have caused clearly bigger operative trauma (ca. 15%) than the other materials.

EXAMPLE 3

Injection molding was applied to manufacture rods ($\phi$=3.2 mm) of the following resorbable polymers: polyglycolide (PGA) ($M_w$=100.000), glycolide/lactide copolymer (PGA/PLA, the molar ratio 87/13, $M_w$=120.000), poly-$\beta$-hydroxybutyrate (PHBA) ($M_w$=500.000) and poly-p-dioxanone (PDS) ($M_w$=300.000).

Polarization microscopy and scanning electron microscopy showed that, exclusive of a thin surface layer, the rods had a spherulitic crystalline structure. The melting points ($T_m$) of the materials of the rods were measured by differential scanning calorimetry (DSC) and the following values were obtained for $T_m$: PGA (225° C.), PGA/PLA (180° C.), PHBA (175° C.) and PDS (110° C.). The tensile strengths of the rods were: PGA (60 MPa), PGA/PLA (50 MPa), PHBA (30 MPa) and PDS (40 MPa). The rods were fibrillated by drawing them at temperatures from room temperature to $T_m$−10° C. to drawing ratios $\lambda$=8–16. The diameters of the fibrillated rods were between 0.8 mm and 1.1 mm. The tensile strengths of the fibrillated rods were: PGA (600 MPa), PGA/PLA (550 MPa), PHBA (400 MPa) and PDS (300 MPa).

EXAMPLE 4

Fibrillated PGA rods of Example 3 and self-reinforced, sintered rods (100 =1.1 mm; which were manufactured of PGA sutures trade name Dexon, size 3-0) which were 50 mm long, were hydrolyzed at 37° C. in distilled water 5 and 7 weeks. The shear load carrying capacities of fibrillated (f) and sintered (s) rods were after manufacturing f: 570N and s: 300N. After hydrolysis of 5 weeks the corresponding values were f: 160N and s: 30N. After 7 weeks hydrolysis the sintered rods had already lost their shear load carrying capacity, but the fibrillated rods showed still 75N shear load carrying capacity.

EXAMPLE 5

Figure 7A:
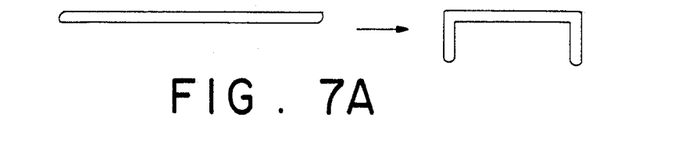
Figure 7B:
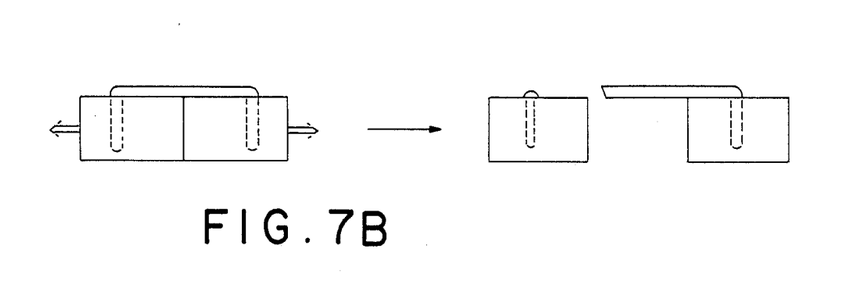

Fibrillated PGA rods of Example 3 (the length 50 mm, $\phi$1.1 mm) were bent in a mold to clamps shown schematically in FIG. 7a in a bending temperature of 180° C. Corresponding self-reinforced clamps were manufactured of PGA sutures (trade name Dexon, size 3-0) by sintering them according to the method of FI Pat. Appl. No. 851828 at elevated temperature and pressure in a clamp mold. The tensile load carrying capacity of fibrillated and sintered clamps was measured by fixing the 10 mm long arms of clamps into holes which were in drawing jaws of a tensile testing machine and by drawing the clamps according to FIG. 7b. The clamps were broken typically according to FIG. 7b from the base of the arm. The fibrillated clamps of this invention showed mean tensile load carrying capacity of 300N and the sintered clamps a corresponding value of 120N.

EXAMPLE 6

Fibrillated PLLA rods n:o 4 of Example 1 were compression molded in a mold with a screw-like mold cavity at about 160° C. temperature to resorbable 30 mm long screws, with the core thickness of 1.1 mm and the height of threads 0.5 mm and the distance between the threads 0.8 mm. The tensile load carrying capacity of the screws was 300N. The corresponding screws which were manufactured by injection molding of PLLA showed a tensile load carrying capacity of 80N and the corresponding self-reinforced, sintered rods which were manufactured of PLLA fibers of Example 1 showed a tensile load carrying capacity of 150N.

EXAMPLE 7

Fibrillated PLLA rods N:o 3 (the length 60 mm, $\phi$1.2 mm) of Example 1 were coated with PDLLA ($M_w$=100.000) by immersing the rods in a 5-% acetone solution of PDLLA and by evaporating the solvent. The operation was repeated so many times that the rods had at last 40 w-% of PDLLA. The coated rods were compressed in a cylindrical mold (the length 60 mm and $\phi$4.5 mm) at 160° C. to cylindrical resorbable rods which showed a bending strength of 450 MPa and a bending modulus of 14 MPa.

EXAMPLE 8

Figure 8A:
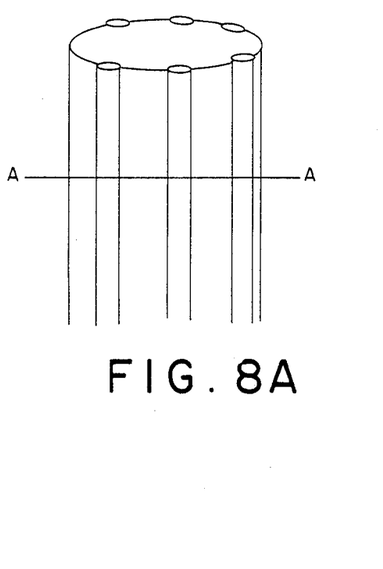
Figure 8B:
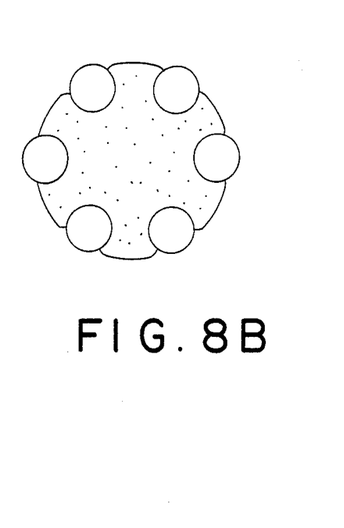
Figure 8C:
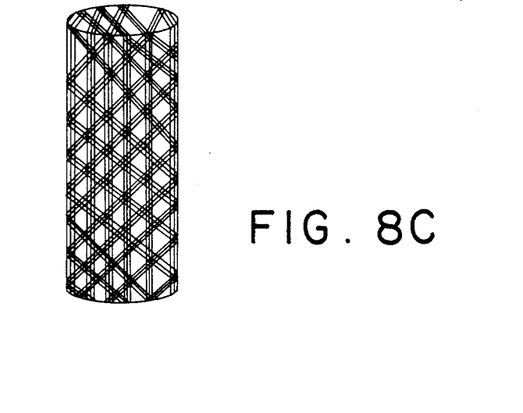

Porous hydroxyapatite (HA-) rods (open porosity about 50%, $\phi$=4 mm and the length 60 mm), which contained on their outer surface 6 longitudinal grooves shown schematically in FIG. 8a and in a crosssectional FIG. 8b (the cross-section plane A—A of FIG. 8a), and resorbable reinforcing materials of this invention were applied to manufacture biocomposite rods (intramedullary nails). The used reinforcing element materials were fibrillated PLLA rods (the length 60 mm, $\phi$1.0 mm) of Example 1. Also PLLA fibre bundles coated with PDLLA (ca. 0.1 mm thick, slightly twisted bundle of fibers; $\phi$ of single fibers 15 $\mu$m and tensile strength 800 MPa) were applied as shown below. A 5-% (w/v) acetone solution of PDLLA ($M_w$=100.000) was spread to the grooves of HA-rods and the fibrillated resorbable rods which were immersed in the same solution were pushed into the grooves. The rods were adhered into the grooves when acetone was evaporated. HA-rods with the fibrillated PLLA rods in their grooves were coated with PLLA fiber bundle (coated with PDLLA) by filament winding method. The filament winding was carried out at 150° C. temperature in such a way that the HA-rods were coated with several fiber bundle layers with different directions so that the fiber bundle layer was, at the most, 0.4 mm thick. The filament winding was carried out in such a way that between fiber bundles remained areas of rod surface without fibers. These uncovered areas of HA-rods could be seen on the surface of biocomposite rods as is shown schematically in FIG. 8c. The resorbable reinforced coating of rods was pressed smooth in a cylindrical mold ($\phi$=5.0 mm). These biocomposites showed a bending strength of 140 MPa, when the bending strength of mere HA-rods was 12 MPa.

The above biocomposite rods were applied to fixation of osteotomies of rabbit femur in the following way. The osteotomy was done with a diamond saw to the uncovered proximal part of rabbit femur about 1 cm from the neck of the femur. The osteotomy was fixed with clamps. A drill hole ($\phi$=5 mm) was drilled through the greater trocanter vertically into the intramedullary channel of femur. The biocomposite rod was tapped into the drill hole so that the upper end of the rod was located on the level of the bone surface. The clamps were removed and soft tissues were closed with a resorbable suture. The animals were returned to their cages and after anesthesia they could move immediately freely. 20 test animals were used. The follow-up time of 6 months showed that all the osteotomies were healed well. Histological examinations of bone-biocomposite test samples showed growth of bone tissue from femoral bone into the open porosity of HA-rods.

We claim:

1. Surgical composite comprising a material selected from the group of resorbable polymer, resorbable copolymer, and mixtures thereof and further containing oriented, at least partially fibrillated structural units (fibrils) which have been induced into the material providing said units while said material is in its original nonfibrillar state by drawing said material in solid state.

2. The surgical composite of claims 1 being in the form of a device selected from the group consisting of rods, plates, screws, nails, tubes and clamps.

3. The surgical composite of claim 1 which contains at least partially ultraoriented structural units.

4. The surgical composite of claim 1 having shear strength value of at least 200 MPa and shear modulus value of at least 4 GPa.

5. The surgical composite of claim 1 having a bending strength value of at least 200 MPa and bending modulus value of at least 4 GPa.

6. The surgical composite of claim 3 having a bending strength value of at least 200 MPa and bending modulus value of at least 4 GPa.

7. The surgical composite of claim 3 having shear strength value of at least 200 MPa and shear modulus value of at least 4 GPa.

8. The surgical composite of claim 1 the composite comprises a matrix and reinforcement fiber that are the same chemically.

* * * * *

REEXAMINATION CERTIFICATE (3701st)
United States Patent
Törmälä et al.

[11] B1 4,968,317
[45] Certificate Issued Jan. 5, 1999

[54] SURGICAL MATERIALS AND DEVICES

[75] Inventors: Pertti Törmälä, Tampere; Pentti Rokkanen; Seppo Vainionpää, both of Helsinki; Juha Laiho, Tampere; Veli-Pekka Heponen, Tampere; Timo Pohjonen, Tampere, all of Finland

[73] Assignee: Biocon Oy, Tampere, Finland

Reexamination Request:
No. 90/004,674, Jun. 23, 1997

Reexamination Certificate for:
Patent No.: 4,968,317
Issued: Nov. 6, 1990
Appl. No.: 250,039
Filed: Oct. 14, 1988

[22] PCT Filed: Dec. 29, 1987
[86] PCT No.: PCT/FI87/00177
§ 371 Date: Oct. 14, 1988
§ 102(e) Date: Oct. 14, 1988
[87] PCT Pub. No.: WO88/05312
PCT Pub. Date: Jul. 28, 1988

[30] Foreign Application Priority Data
Jan. 13, 1987 [FI] Finland ................... 870111

[51] Int. Cl.$^6$ ............................................. A61B 17/58
[52] U.S. Cl. ................................................ 606/77; 606/76

[58] Field of Search ........................................ 606/76, 77

[56] References Cited

U.S. PATENT DOCUMENTS

| | | | |
|---|---|---|---|
| 4,052,988 | 10/1977 | Doddi | 128/335.5 |
| 4,141,087 | 2/1979 | Shalaby | 3/1 |
| 4,612,923 | 9/1986 | Kronenthal | 606/777 |
| 4,671,280 | 6/1987 | Dorband | 128/334 |

FOREIGN PATENT DOCUMENTS

| | | | |
|---|---|---|---|
| 0 202 090 | 11/1986 | European Pat. Off. | A61B 17/08 |
| 0 204 931 | 12/1986 | European Pat. Off. | A61L 31/00 |

OTHER PUBLICATIONS

Ward, I.M., *Structure and Properties of Oriented Polymers*, Applied Science Publishers, Ltd., pp. ix to xv and Chapters 1, 2, and 7., Date Unknown.

Getter, L. et al., *A biodegradable Intraosseous Appliance in the Treatment of Mandibular Fractures*, 1972, Journal of Oral Surgery, 30, pp. 344–348.

Greve, H. and Holste, J., *Refixation Osteochondraler Fragmente durch Resorbierbare Kunststoffstifte*, 1985, Akt. Traumatol, 15, pp. 145–149.

(List continued on next page.)

*Primary Examiner*—Michael Buiz

[57] ABSTRACT

Surgical material of resorbable polymer, copolymer, or polymer mixture containing at least partially fibrillated structural units, and use thereof.

OTHER PUBLICATIONS

Greve, H. and Holste, J., *Synthetisches Resorbierbares Material zur Refixation von Kleinen Knochernen Fragmenten oder Sehnen–bzw,* 1985, Bandausrissen im Tierexperiment, Chirurgisches Forum '85, Springer–Verlag.

Claes, L. et al., *Resorbierbare Implantate zur Refixierung von Osteochondralen Fragmenten in Gelenkflachen,* 1986, Aktuelle Traumatologie, 2, pp. 16, 43–82.

Haas, H.–G., *PDS–Splinte zur Frakturbehandlung,* 1986, Handchirurgie, 18, pp. 295–297.

Rustemeier, M. and Ganssmann, M., *Versorgung von Knockernen Strecksehnenabrissen mit Resorbierbaren Materialien,* 1986, Handchirurgie, 18, pp. 302–303.

Ray, J. A. etal., *Polydioxanone (PDS), A Novel Monofilament Synthetic Absorbable Suture,* 1981, Surg., Gyn., & Obstet., 153, pp. 497–507.

Niederdellmann, H. and Buhrmann, K., *Resorbierbare Osteosyntheseschrauben aus Polydioxanon (PDS),* 1983, Dtsch. Z., Mund–Kiefer–Gesichts–Chir., 7, pp. 399–400.

Dumbach, J., and Ergebnisse, Erst, *Zugschraubenosteosynthese nach Ramusosteotomie mit Resorbierbaren Osteosyntheseschrauben aus Polydioxanon (PDS),* 1984, Dtsch. Z., Mund–Kiefer–Gesichts–Chir., 2, pp. 145–148.

Gay, B. and Bucher, H., *Tierexperimentelle Untersuchungen zur Anwendung von Absorbierbaren Osteosyntheseschrauben aus Polydioxanon (PDS),* 1985, Unfallchirurg., 88, pp. 126–133.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 3 and 4-8 are cancelled.

Claim 2 is determined to be patentable as amended.

New claims 9-17 are added and determined to be patentable.

2. [The surgical composite of claims 1] *Surgical device comprising a material selected from the group of resorbable polymer, resorbable copolymer, and mixtures thereof said material being drawn in solid state to a composite containing oriented, at least partially fibrillated structural units, wherein the drawn composite is formed into a bone surgery* device being in the form [of a device] selected from the group consisting of rods, plates, screws, nails, tubes, and clamps.

*9. Surgical device comprising a material selected from the group of resorbable polymer, resorbable copolymer, and mixtures thereof, said material being drawn in solid state to a composite containing oriented, at least partially fibrillated structural units, wherein the drawn composite is formed into the device, said device having a segment having an at least partially fibrillated profiled surface.*

*10. Surgical device of claim 9 in which the device is a bone surgery device.*

*11. Surgical device of claim 10 having a bending strength value of at least 200 MPa and bending modulus value of at least 4 GPa.*

*12. Surgical device of claim 10 having shear strength value of at least 200 MPa and shear modulus value of at least 4 GPa.*

*13. Surgical device of claim 9 in which the device is a screw.*

*14. Surgical device of claim 9 in which the profiled surface comprises barbs.*

*15. Surgical device of claim 9 in which the resorbable polymer is polylactic acid.*

*16. Surgical device of claim 9 in which the resorbable polymer is polyglycolic acid.*

*17. Surgical device of claim 9 in which the resorbable copolymer comprises polylactic acid and polyglycolic acid.*

* * * * *